(12) United States Patent
Murray et al.

(10) Patent No.: US 9,226,755 B2
(45) Date of Patent: Jan. 5, 2016

(54) STYLUS ASSEMBLY

(75) Inventors: David Wycliffe Murray, Oxford (GB); Christopher Alexander Dodd, Oxford (GB); John William Goodfellow, Basingtoke (GB); John Joseph O'Connor, Oxford (GB); Russell Lloyd, Wiltshire (GB)

(73) Assignee: BIOMET UK LIMITED, South Wales (GB)

( * ) Notice: Subject to any disclaimer, the term of this patent is extended or adjusted under 35 U.S.C. 154(b) by 998 days.

(21) Appl. No.: 13/389,894

(22) PCT Filed: Aug. 3, 2010

(86) PCT No.: PCT/GB2010/051275
§ 371 (c)(1),
(2), (4) Date: May 23, 2012

(87) PCT Pub. No.: WO2011/018647
PCT Pub. Date: Feb. 17, 2011

(65) Prior Publication Data
US 2012/0245588 A1 Sep. 27, 2012

(30) Foreign Application Priority Data
Aug. 12, 2009 (GB) .................................. 0914116.9

(51) Int. Cl.
*A61B 17/15* (2006.01)
*A61B 17/17* (2006.01)

(52) U.S. Cl.
CPC ............. *A61B 17/154* (2013.01); *A61B 17/155* (2013.01); *A61B 17/157* (2013.01); *A61B 17/1764* (2013.01)

(58) Field of Classification Search
CPC ...... A61B 17/17; A61B 17/15; A61B 17/154; A61B 17/155
See application file for complete search history.

(56) References Cited

U.S. PATENT DOCUMENTS

| 5,704,941 A | 1/1998 | Jacober et al. |
| 2003/0100906 A1* | 5/2003 | Rosa et al. .................... 606/86 |

FOREIGN PATENT DOCUMENTS

| EP | 1 723 916 A1 | 11/2006 | |
| GB | 2 426 198 A | 11/2006 | |
| GB | 2426198 A * | 11/2008 | ............. A61B 17/15 |
| WO | WO-03045256 A2 | 6/2003 | |

OTHER PUBLICATIONS

International Search Report for PCT/GB2010/051275, mailed Nov. 15, 2010; ISA/EP.

* cited by examiner

*Primary Examiner* — Christian Sevilla
(74) *Attorney, Agent, or Firm* — Schwegman Lundberg & Woessner, P.A.

(57) ABSTRACT

A stylus assembly (10) adapted to align a surgical tool with a bone, the stylus assembly (10) comprising: a mounting element (12,18); a tool guide (50) adjustably mounted relative to the mounting element (12,18); a stylus (16) adjustably mounted relative to the mounting element (12,18) and having a curved portion for engagement with a predetermined part of the bone; and a lockable retaining member (14) for simultaneously locking the surgical tool guide (50) and the stylus (16) to the mounting element (12,18).

22 Claims, 3 Drawing Sheets

STYLUS ASSEMBLY

CROSS-REFERENCE TO RELATED APPLICATIONS

This application is a 371 U.S. National Stage of International Application No. PCT/GB2010/051275, filed Aug. 3, 2010, and claims priority to British patent application No. 0914116.9 filed Aug. 12, 2009, the disclosures of which are herein incorporated by reference in their entirety.

The present invention relates to an instrument for sizing bone and particularly but not exclusively to a stylus assembly for use in positioning a surgical tool guide used in the resection of a proximal human tibia.

BACKGROUND

It is known to provide a surgical tool guide having a resection guide, which assists a surgeon in making accurate and repeatable cuts during surgery. The accuracy of a cut made using a resection guide is mainly determined by the successful positioning and fastening of the guide in the operative area. Typically, a stylus is attached to the guide, which references from a reference point or marker on the body, for example, a bone. The stylus is either free to translate and/or rotate relative to the guide, so that it may be adjusted, or is rigidly fixed to the guide. An attachment mechanism mounts the stylus to the guide, and a locking mechanism locks the stylus in a desired position relative to the attachment mechanism and hence the guide. Once in the operating position, the guide can be attached to, for example, a bone using pins and/or bone screws.

It is also known to use a stylus to position a guide in joint replacement surgery. For example, during a total or partial knee replacement operation, it is necessary to resect the proximal tibia to a specific level. Existing tibial styli reference from the tibial plateau. This area of the joint is subject to considerable wear and, in a knee requiring joint replacement is likely to be damaged. Therefore, the tibial plateau does not provide a reliable reference position.

Once a stylus has been used to position a guide, it is usually removed, in order to increase the working space available to the surgeon. A problem of existing arrangements is that the removal of the stylus can cause unintentional and unnoticed movement of the cutting guide. This leads to inaccurate positioning of the cutting guide, with the result that the surgeons' incisions are misdirected.

GB 2426198 discloses a stylus assembly which has a stylus that references from the posterior femoral condyle which provides a relatively unworn reference surface. The stylus assembly is easily removed from a guide in order to prevent unwanted movement of the guide.

Whilst the stylus used in the assembly of GB 2426198 provides a reference point for performing a repeatable resection of the tibial plateau, it does not provide any feedback regarding the condition of the joint surfaces and that of the ligaments in the knee. The present invention seeks to address this issue.

STATEMENTS OF INVENTION

According to the present invention there is provided a stylus assembly adapted to align a surgical tool with a bone, the stylus assembly comprising:
 a mounting element;
 a tool guide adjustably mounted relative to the mounting element;
 a stylus adjustably mounted relative to the mounting element and having a curved portion for engagement with a predetermined part of the bone; and
 a lockable retaining member for locking the surgical tool guide and the stylus to the mounting element.

The stylus may have a curvature which corresponds to the articular geometry of a surgical implant.

The stylus may further comprise a handle portion attached to the curved portion.

The curved portion of the stylus may extend past an end of the handle portion to form a protrusion or anterior extension of the stylus. The anterior extension of the stylus may detail the position of cartilage if it had not been eroded and provide a surgeon with an indication of the natural aspect of a healthy bone.

The protrusion may comprise an indicator which indicates the correct position for implanting a fixation peg of a surgical implant.

The mounting element may further comprises a body, the body having first and second arms with a space therebetween for receiving a portion of the surgical tool guide, wherein actuation of the lockable retaining member from an unlocked to a locked position moves the retaining member axially and causes the body to bear against the surgical tool guide and lock it relative to the body.

The lockable retaining member may extends from and be fixed to the first arm of the body.

The lockable retaining member may have an enlarged head at its free end, and the stylus may have a slotted portion. The slotted portion of the stylus may be mounted about the retaining member, enabling translational and rotational movement of the stylus relative to the body in the unlocked position of the lockable retaining member.

The mounting element may further comprise a bifurcated intermediate element having first and second arms through which the lockable retaining member passes.

A portion of the first arm of the intermediate element may be positioned between the body and the stylus and the lockable retaining member may pass through an aperture in the first arm of the intermediate element.

The second arm of the intermediate element may extend into the space between the first and second arms of the body.

The first arm of the body may extend into in a space between the first and second bifurcated arms of the intermediate element.

A first clearance may be provided between the second arm of the intermediate element and the said first arm of the body, and a second clearance may be provided between the retaining head of the retaining member and the stylus, the first clearance being greater than the second clearance.

The lockable retaining member may be moved between the locked and the unlocked positions by means of a cam which is pivotally mounted to the body.

A surface of the stylus which abuts the mounting element may be substantially parallel to a tool guide surface formed on the tool guide.

The curved portion may have a substantially spherical bone engaging surface. The curved portion may be adapted to engage a particular region of bone. For example, it may be shaped such that when correctly aligned the free end of the curved portion contacts the posterior femur. In another embodiment, the posterior aspect of the stylus substantially replicates the posterior aspect of the femur.

According to another aspect of the present invention there is provided a stylus assembly kit comprising a mounting element for aligning and fixing a surgical tool guide relative to a bone and a plurality of styli which are selectively connectable to the mounting element, wherein the plurality of styli are of different dimensions. For example, at least the curved portions of the styli may be of different thicknesses.

The kit may also comprise a plurality of mounting elements of different dimensions to adapt the stylus assembly for use with a particular patient. For example, the kit may comprise a plurality of mounting elements of different heights, so that by changing one mounting element for another of the mounting elements in the kit, the selected stylus is spaced a different distance from the tool guide.

According to another aspect of the present invention there is provided a method of aligning and fixing a surgical tool guide relative to a first bone which articulates with a second bone at a joint, the method comprising the steps of:
inserting the curved portion of a stylus, having a handle portion and a curved portion, between said first and second bones, such that a free end of the curved portion contacts a desired region of the first bone;
locking a tool guide to the handle portion of the stylus by means of a lockable mounting element, such that the tool guide is correctly aligned with the first bone; fixing the tool guide to the first bone;
disconnecting the mounting element and stylus from the tool guide: and
resecting the first bone by reference to the tool guide.

The step of inserting the curved portion of the stylus between said first and second bones may be repeated with styli having different thickness and/or offset between the handle portion and the curved portion and/or differently shaped or dimensioned portions or spacers which have the effect of changing the resultant laxity in the joint, the method further comprising the step of selecting the stylus which provides the desired laxity, before the step of locking the tool guide to the handle portion.

The step of locking a tool guide to the handle portion of the stylus by means of a lockable mounting element, may comprise the step of selecting an appropriate size of lockable mounting element to correspond to a desired thickness of bearing element to fit a particular patient.

BRIEF DESCRIPTION OF THE DRAWINGS

For a better understanding of the present invention, and to show more clearly how it may be carried into effect, reference will now be made, by way of example, to the accompanying drawings, in which:—

DETAILED DESCRIPTION

Figure 1:
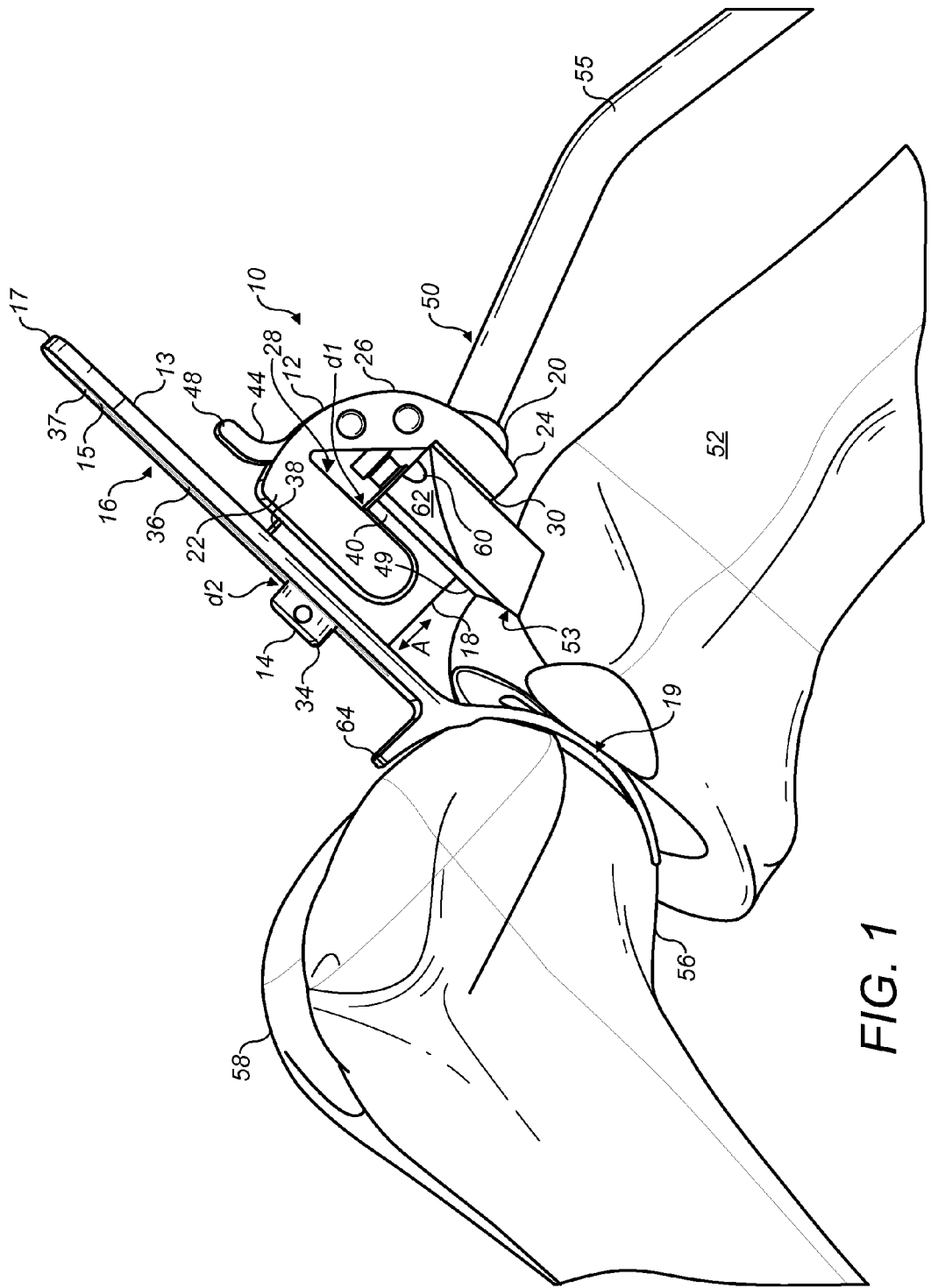
FIG. 1 is a side view of a stylus assembly in accordance with the invention, wherein the stylus assembly is in use and secured to a surgical guide.

Referring firstly to FIG. 1, a clamp assembly is indicated generally at 10. The clamp assembly 10 can be made from stainless steel, metal alloy, any suitable material such as plastics or any combination of these and/or other materials.

The clamp assembly 10 comprises a substantially C-shaped body 12, a retaining member 14 attached to the body 12, a stylus 16, mounted about and retained by the retaining member 14, an intermediate element 18, and a locking member 20, for securing the clamp assembly 10 to a surgical tool guide 50.

The stylus 16 has an elongate "handle" portion 17 and a curved "bowl" portion 19. Both the top and bottom surfaces of the curved portion 19 are substantially spherical, but any suitable continuous or discontinuous curved surfaces are contemplated dependent on the joint to which the invention is applied. The curvature of the bowl portion 19 corresponds to the articular geometry of a bearing element of a prosthesis (not shown). The elongate portion 17 is flat and is used to mount the stylus 16 to the retaining member 14.

The stylus 16 has a curved protrusion 64 which comprises the proximal end of the bowl portion 19. The curved protrusion 64 acts as an indicator which identifies to the surgeon the correct position for the primary peg of the femoral implant and the flexion angle achieved.

The C-shaped body 12 has a first arm 22, which is the upper arm as viewed in the drawings, a second lower arm 24 and a central portion 26 connecting the first and second arms 22, 24 together. The inner surfaces 28, 30 of the arms 22, 24, i.e. the surfaces facing one another, define a space 23 therebetween for receiving part of the surgical tool guide 50.

The retaining member 14 may be a pin or screw or other suitable fixing, which extends at right angles through the first arm 22 of the body 12 and has an enlarged head 34.

Figure 2:
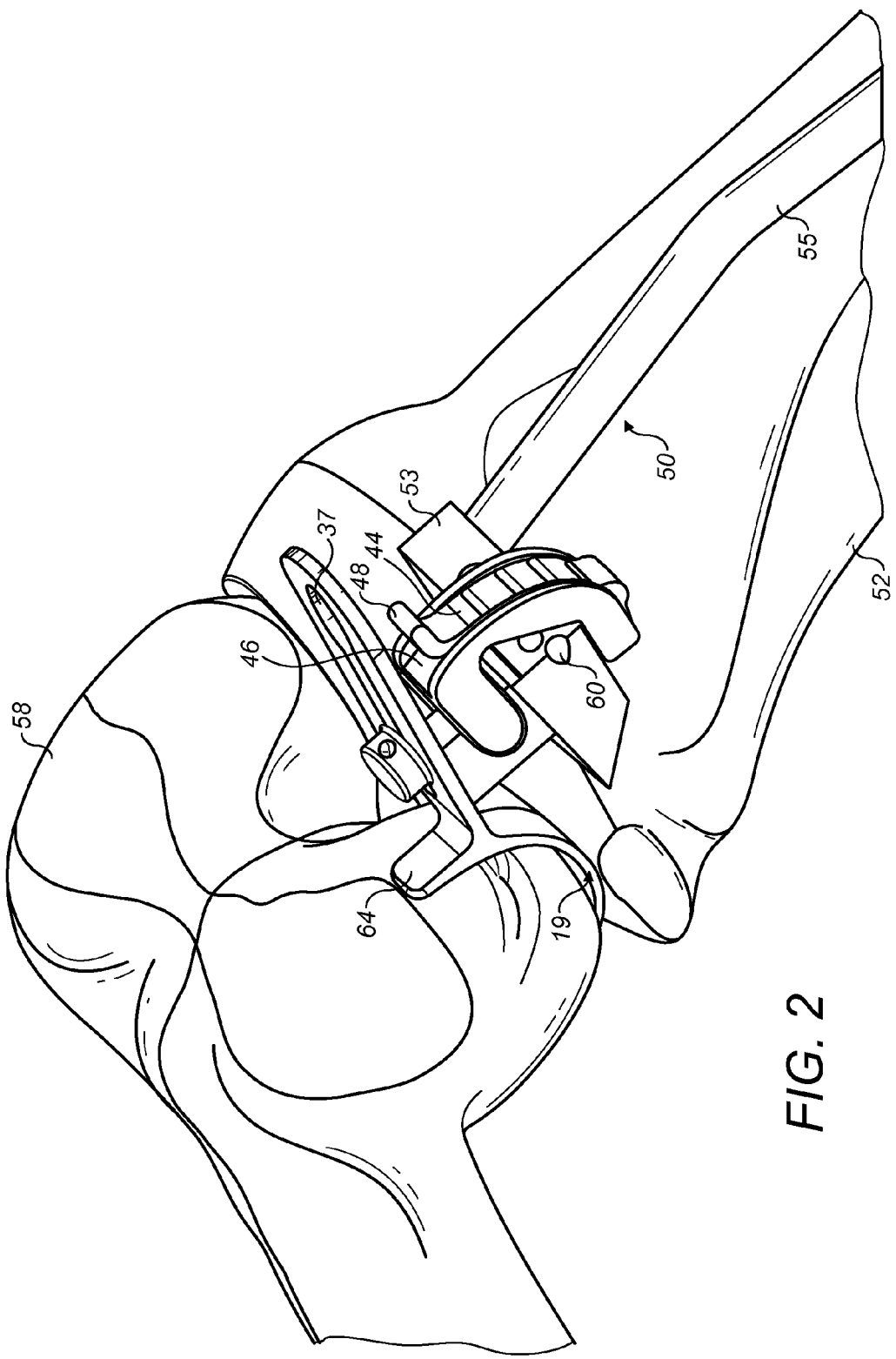
FIG. 2 is a second perspective view of the stylus assembly of FIG. 1.

The elongate portion 17 of the stylus 16 has a substantially planar lower surface 13 and a substantially planar upper surface 15 such that the elongate portion 17 has the form of a flat plate. The elongate portion 17 has a longitudinal slot 36 running therethrough, which has an enlarged portion 37 at one end sized to accommodate the head 34 of the retaining member 14. The retaining member 14 is located within the slot 36 as a clearance fit, thus enabling translation and rotation of the stylus 16 about the pin 14. The stylus 16 is retained on the retaining member 14 by the enlarged head 34 which is introduced through the enlarged portion 37 (as shown in FIG. 2) of the longitudinal slot 36 and then translated to retain the stylus 16.

The intermediate element 18 is bifurcated and has first and second arms 38, 40, which are disposed one either side of the first arm 22 of the body 12. An aperture is provided through the first arm 38 of the intermediate element 18, through which the retaining member 14 passes. The stylus 16 is disposed above the first arm 38 of the intermediate element (as viewed in the drawings) between the intermediate element 18 and enlarged head 34. The upper surface of the first arm 38 provides a planar reference surface over which the lower surface 13 of the stylus 16 is able to translate and rotate.

The second arm 40 of the intermediate element 18 extends into the space 23 between the first and second arms 22, 24 of the body 12. In other words, the first arm 22 of the body 12 is disposed between the first and second arms 38, 40 of the intermediate element 18.

The locking member 20 is a cam, which is pivotally mounted to the second arm 24 of the body 12. A cam lever 44 is integrally formed with the cam, the cam protruding into the space 23 between the first and second arms 22, 24 of the body 12, when actuated to a locked position.

The surgical tool guide 50 comprises a support rod 55 having a guide block 53 at one end and an attachment plate (not shown) at the opposite end. The attachment plate is slideably mounted on the support rod and may be fixed at a desired position to be clamped to a limb of a patient. In the illustrated embodiment the attachment plate is clamped to a shin of a patient, although in alternative embodiments, another limb or another part of the leg may be clamped.

The guide block 53 is fixed to the support rod 55 and comprises one or more drill guide holes, saw guide slots and/or fixing holes 60. Chamfered edges 62 (as shown in FIG.

1) are provided to facilitate the insertion of fixings such as pins or screws through the holes 60 in the guide block 53.

As shown in FIG. 2, a slot or channel 46 is provided in the rear edge of the body 12, which receives the cam lever 44 when the lever is in a locked position. An end portion 48 of the cam lever 44 extends out of the channel 46 so the cam leaver 44 can be rotated easily using a thumb and index finger away from the body 12 into an unlocked position.

The central portion 26 of the body 12 has an inner surface, between the arms 22, 24, which acts as a stop, against which the guide block 53 of the surgical tool guide 50 can rest.

Figure 3:
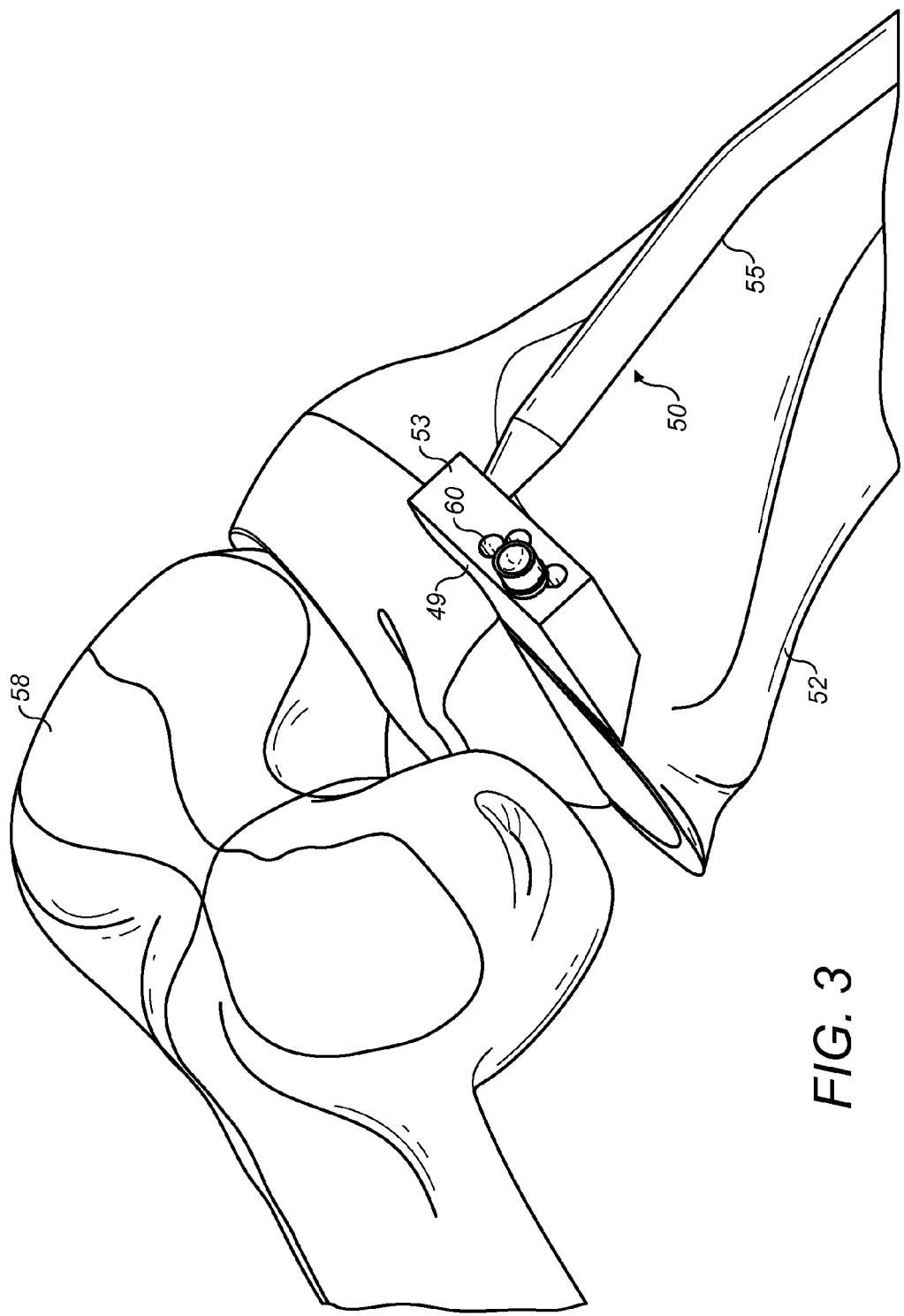
FIG. 3 shows the tool guide of FIG. 2 following removal of the stylus assembly and resection of the bone.

As shown in FIGS. 1 and 3, an upper surface of the guide block 53 comprises a planar saw guide surface 49 which is parallel to the elongate portion 17 of the stylus 16 and may also be parallel to the fixing holes 60, although these fixing holes may be offset where this provides more secure attachment of bone screws or other fixing into the tibia.

The intermediate element 18 is able to move a short distance vertically, as indicated by arrow A in FIG. 1, relative to the body 12. A first clearance d1 is provided between the upper surface of the second arm 40 of the intermediate element and the lower surface of the first arm 22 of the body 12. A second clearance d2 is provided between the underside of the head 34 and the upper surface of the elongate portion 17 of the stylus 16. The first clearance d1 is greater than the second clearance d2, thereby causing movement of the intermediate element 18, under the action of the cam lever 44, towards the head 34 until the stylus 16 is trapped between the underside of the head 34 and the first arm 38 of the intermediate element 18.

In use, the clamp assembly 10 is used to position the guide 50 relative to the tibia. In FIG. 2, the guide 50 is shown attached to a patient's tibia 52, by means of, for example, pins or bone screws, for performing a resection of the proximal tibia (i.e. the tibial plateau) in a knee operation. It will be appreciated that the invention can be applied to other joints in a human or animal body, and that the guide 50 could be fixed to another limb or to another part of the leg by any suitable means.

In order to fix the guide 50 to the tibia 52, it is necessary first to select an appropriate stylus to achieve as closely as possible the natural ligament tension. To achieve this, styli of different thickness are inserted in turn into the gap between the femur and tibia with the joint at approximately 90° of flexion. Insertion of the bowl portion 19 of the stylus 16 into this gap distends the joint, spacing the femur 58 and tibia 52 away from one another. If there is too much laxity in the joint, the stylus 16 is removed and replaced with a thicker stylus 16. To facilitate this trialling process, the surgeon is provided with a set of styli 16 which have bowl portions 19 of different thicknesses. For example, styli may be provided having bowl portions of 1 mm, 2 mm and 3 mm thickness respectively. For each patient, the thickness of the bowl portion 19 is selected so that resection takes up the desired amount of the laxity in the ligaments of the knee. The thickness of the bowl portion 19 which is selected provides a measure of the articular cartilage erosion from the distal femur and tibial plateau.

It will be appreciated that placing a thicker stylus between the femur and the tibia causes the tibia 52 to be translated down relative to the guide block 53 and thus results in less of the tibia 52 being resected. This provides a tighter fit for the prosthesis and reduces the laxity in the joint.

Once the correct stylus has been selected, it is attached to the retaining member by inserting the head 34 of the retaining member 14 in the slot 36. The stylus 16 is then adjusted about the retaining member 14 until the free end of the bowl portion 19 is located against the surface of the posterior femoral condyle 56. This surface of the posterior femoral condyle provides a reference surface of relatively unworn bone. The degree of movement between the elements of the clamp assembly 10 in the unlocked condition facilitates the positioning of the stylus 16 between the tibia 52 and femur 58 through the operative wound. Alternatively, the stylus 16 may be inserted into the operative wound prior to mounting of the stylus 16 on the retaining member 14.

The chamfered edges 62 of the guide block 53 allow the clamp assembly 10 to be rotated relative to the guide block 53. Therefore the guide block 53 and stylus 16 may be aligned properly, whilst the clamp assembly 10 is angled to allow access to the holes 60. Alternatively the body 12 may be dimensioned in such a manner to allow rotation of the clamp assembly 10 about the guide block 53 so that the chamfered edges 62 are not necessary.

Once the guide block 53 is positioned relative to the tibia, the cam lever 44 is rotated to the locked position, which causes the cam 20 to extend into the space 23. This clamps the guide block 53 between the cam 20 and the second arm 40 of the intermediate element 18. In so doing, the intermediate element is forced upwards, as viewed in the drawings, towards the head 34 of the retaining member 14, and the first arm 38 of the intermediate element 18 clamps the stylus 16 against the enlarged head 34.

The guide block 53 is then fixed to the tibia by means of bone screws which are screwed into the tibia through the fixing holes in the guide block 53.

With the guide block correctly aligned and fixed to the tibia the clamp assembly 10 can be removed from the guide block 53 by rotating the cam lever 44 downwards to its unlocked position, which causes the cam 20 to retract into the channel 46 of the body 12 thereby releasing the clamp assembly from the guide block 53. The clamp assembly 10 and guide block 53 are dimensioned so that the guide block 53 has only a small amount of play in the space 23 of the body 12 when in the unlocked condition. This is so that the range of axial movement of the cam 20 in the space 23 can be minimised, and so that the range of movement of the stylus 16 is also minimised. For example, the range of axial movement of the cam may be 0.25 to 2 mm, or more preferably about 1 mm. If the guide block 53 is too small to substantially fill the space 23, the intermediate element 18 may not be displaced sufficiently to lock the stylus 16. This problem can be addressed by increasing the effective thickness of the guide block 53, by means of one or more shims (not shown).

With the clamp assembly removed the surgeon can access the guide block 53 with ease and make the necessary resection of the tibia by aligning a surgical saw with the planar saw guide surface 49.

FIG. 3 shows the tibia 52 following resection, with the guide block 53 attached. The level of the resection can be adjusted by selecting a stylus 16 of a different thickness, as mentioned above and/or by the method described in more detail below.

The thickness of the intermediate element 18 corresponds to the thickness of the bearing which will be used in the prosthesis. Several clamp assemblies 10 may be provided which correspond to the different bearings and the appropriate clamp assembly 10 and bearing should be chosen for a particular patient. For example, a heavier patient may require a thicker bearing and thus a clamp assembly having a thicker intermediate element will be used. This causes the guide block 53 to be positioned lower on the tibia 52, so that more of the bone is resected.

The stylus 16 is curved to replicate the articular geometry of a bearing element of a femoral implant. As a result of this curvature, even if the femur is not at exactly 90 degrees to the tibia, the stylus 16 will fit the femur accurately and will reference accurately off the posterior aspect of the distal femur.

It will be appreciated that, as the proximal end of the bowl portion 19 of the stylus 16 is curved, disruption of cartilage is minimized when the bowl portion 19 is inserted into the joint. By contrast, if a flat stylus is used in place of the above mentioned stylus with a bowl portion 19, it would only contact the distal femur and tibial plateau at their highest points. A flat stylus therefore does not enable a surgeon to take into account erosion of the articular cartilage when assessing the laxity in the joint.

In the above described embodiment a plurality of styli are provided having different thickness. However the required laxity in the joint may be achieved by providing styli having differently shaped or dimensioned portions or spacers.

The invention claimed is:

1. A stylus assembly adapted to align a surgical tool with a bone, the stylus assembly comprising:
    a mounting element;
    a surgical tool guide adjustably mounted relative to the mounting element;
    a stylus adjustably mounted relative to the mounting element and having a curved portion for engagement with a predetermined part of the bone and a handle portion attached to the curved portion, wherein the curved portion extends past an end of the handle portion to form a protrusion; and
    a lockable retaining member for locking the surgical tool guide and the stylus to the mounting element.

2. The stylus assembly as claimed in claim 1, wherein the stylus has a curvature which corresponds to the articular geometry of a surgical implant.

3. The stylus assembly as claimed in claim 1, wherein the protrusion comprises an indicator which indicates the correct position for implanting a fixation peg of a surgical implant.

4. The stylus assembly as claimed in claim 1, wherein the mounting element further comprises a body, the body having first and second arms with a space therebetween for receiving a portion of the surgical tool guide, wherein actuation of the lockable retaining member from an unlocked to a locked position moves the retaining member axially and causes the body to bear against the surgical tool guide and lock it relative to the body.

5. The stylus assembly as claimed in claim 4, wherein the lockable retaining member extends from the first arm of the body.

6. The stylus assembly as claimed in claim 5, wherein the lockable retaining member has an enlarged head at its free end.

7. The stylus assembly as claimed in claim 6, wherein the stylus has a slotted portion.

8. The stylus assembly as claimed in claim 7, wherein the slotted portion of the stylus is mounted about the retaining member, enabling translational and rotational movement of the stylus relative to the body in the unlocked position of the lockable retaining member.

9. The stylus assembly as claimed in claim 5, wherein the mounting element further comprising a bifurcated intermediate element having first and second arms through which the lockable retaining member passes.

10. The stylus assembly as claimed in claim 9, wherein a portion of the first arm of the intermediate element is positioned between the body and the stylus.

11. The stylus assembly as claimed in claim 10, wherein the second arm of the intermediate element extends into the space between the first and second arms of the body.

12. The stylus assembly as claimed in claim 11, wherein the first arm of the body extends into in a space between the first and second bifurcated arms of the intermediate element.

13. The stylus assembly as claimed in claim 12, wherein a first clearance is provided between the second arm of the intermediate element and the first arm of the body, and a second clearance is provided between a retaining head of the retaining member and the stylus, the first clearance being greater than the second clearance.

14. The stylus assembly as claimed in claim 1, wherein the lockable retaining member clamps the stylus between locked and unlocked positions by moving a cam which is pivotally mounted to the body.

15. The stylus assembly as claimed in claim 1, wherein a surface of the stylus which abuts the mounting element is substantially parallel to a tool guide surface formed on the tool guide.

16. The stylus assembly as claimed in claim 1, wherein the curved portion has a substantially spherical bone engaging surface.

17. A stylus assembly kit adapted to align a surgical tool with a bone, the stylus assembly kit comprising:
    a mounting element;
    a surgical tool guide adjustably mounted relative to the mounting element;
    a stylus adjustably mounted relative to the mounting element and having a curved portion for engagement with a predetermined part of the bone;
    a lockable retaining member for locking the surgical tool guide and the stylus to the mounting element; and
    at least one additional stylus, the styli being of different thicknesses at least over the curved portion.

18. The stylus assembly kit as claimed in claim 17 further comprising at least one additional mounting element, the mounting elements being of different heights, so that by selecting a different mounting element the selected stylus is spaced a different distance from the tool guide.

19. A method of aligning and fixing a surgical tool guide relative to a first bone which articulates with a second bone at a joint, the method comprising:
    inserting a curved portion of a stylus, having a handle portion wherein the curved portion extends past an end of the handle portion to form a protrusion between said first and second bones, such that a free end of the curved portion contacts a desired region of the first bone;
    locking a tool guide relative to the handle portion of the stylus by a lockable retaining member extending from a mounting element, such that the tool guide is correctly aligned with the first bone;
    fixing the tool guide to the first bone;
    disconnecting the mounting element and stylus from the tool guide: and
    resecting the first bone by reference to the tool guide.

20. The method of claim 19, wherein inserting the curved portion of the stylus between said first and second bones is repeated with styli having different dimensions.

21. The method of claim 19 further comprising selecting a stylus which provides a desired laxity, before the step of locking the tool guide to the handle portion.

22. The method of claim 19, wherein locking a tool guide to the handle portion of the stylus by the lockable retaining member and mounting element includes selecting an appropriate size of mounting element to correspond to a desired thickness of bearing element to fit a particular patient.

\* \* \* \* \*